(12) United States Patent
Karin et al.

(10) Patent No.: US 7,319,134 B2
(45) Date of Patent: Jan. 15, 2008

(54) REGULATION OF TRANSCRIPTION FACTOR, NF-IL6/LAP

(75) Inventors: Michael Karin, San Diego, CA (US); Christian Trautwein, Hannover (DE)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 10/162,141

(22) Filed: Jun. 3, 2002

(65) Prior Publication Data
US 2007/0275440 A1 Nov. 29, 2007

Related U.S. Application Data

(60) Continuation of application No. 09/080,633, filed on May 18, 1998, now abandoned, which is a division of application No. 08/436,874, filed on May 8, 1995, now Pat. No. 5,874,209, which is a division of application No. 08/096,177, filed on Jul. 20, 1993, now abandoned.

(51) Int. Cl.
| A61K 38/00 | (2006.01) |
| C07K 14/00 | (2006.01) |
| C07K 16/00 | (2006.01) |
| C07K 17/00 | (2006.01) |
| C07K 2/00 | (2006.01) |
| C07K 4/00 | (2006.01) |
| C07K 5/00 | (2006.01) |

(52) U.S. Cl. .................. 530/300; 530/350; 435/4; 435/7.2; 435/194; 436/86

(58) Field of Classification Search ............. 455/4, 455/7.2, 194; 530/300, 350; 436/86
See application file for complete search history.

(56) References Cited

FOREIGN PATENT DOCUMENTS

WO    WO 91/08774    6/1991

OTHER PUBLICATIONS

Lazar et al. Molecular and Cellular Biology 8(3): 1247-1252, Mar. 1988.*
GenCore Database sheet, Sequence alignment between Applicants' sequence ID No. 1 and Chang and Akira sequences, 1 sheet.*
GenCore database alignment between Applicants' SEQ ID No. 1 and SEQ ID No. 4 with Chang et al. (Dec. 1990) and Akira et al (1990).*
Amino acid database, GenCore. Sequence alignment between instant application's SEQ ID No. 1 and Descombes et al. Genes Dev. 4: 1541-1551, 1990/ IDS reference, AE submitted Sep. 16, 2002.*
Amino acid database, GenCore. Sequence alignment between instant application's SEQ ID No. 4 and Chang et al. Molecular and Cellular Biology 10(12): 6642-6653, Dec. 1990/ Reference AC from IDS submitted Sep. 16, 2002.*
Amino acid database, GenCore. Sequence alignment between instant application's SEQ ID No. 1 and Poli et al. Cell 63: 643-653, Nov. 2, 1990/ IDS reference, AG Submitted Sep. 16, 2002.*
Akira et al., "A Nuclear Factor for IL-6 Expression (NF-IL6) is a Member of a C/EBP Family," *The EMBO Journal*, 9(6):1897-1906, Oxford University Press (1990).
Chang et al., "Molecular Cloning of a Transcription Factor, AGP/EBP, That Belongs to Members of the C/EBP Family," *Molecular and Cellular Biology*, 10(12):6642-6653, American Society for Microbiology (1990).
Descombes and Schibler, "A Liver-Enriched Transcriptional Activator Protein, LAP, and a Transcriptional Inhibitory Protein, LIP, are Translated from the Same mRNA," *Cell*, 67:569-579, Cell Press (1991).
Descombes et al., "LAP, a Novel Member of the C/EBP Gene Family, Encodes a Liver-Enriched Transcriptional Activator Protein," *Genes & Development*, 4:1541-1551, Cold Spring Harbor Laboratory Press (1990).
Köhler and Milstein, "Continuous Cultures of Fused Cells Secreting Antibody of Predefined Specificity," *Nature*, 256:495-497 (1975).
Poli et al., "IL-6DBP, a Nuclear Protein Involved in Interleukin-6 Signal Transduction, Defines a New Family of Leucine Zipper Proteins Related to C/EBP," *Cell*, 63:643-653, Cell Press (1990).
Ron and Habener, "CHOP, a Novel Developmentally Regulated Nuclear Protein that Dimerizes with Transcription Factors C/EBP and LAP and Functions as a Dominant-Negative Inhibitor of Gene Transcription," *Genes & Development*, 6:439-453, Cold Spring Harbor Laboratory Press (1992).
Trautwein et al., "Transactivation by NF-IL6/LAP is Enhanced by Phosphorylation of its Activation Domain," *Nature*, 364:544-547 (1993).

\* cited by examiner

*Primary Examiner*—Alana M. Harris
(74) *Attorney, Agent, or Firm*—DLA Piper US LLP

(57) ABSTRACT

An alteration in phosphorylation of serine 105, within the activation domain of NF-IL6/LAP, alters its transcriptional efficacy. Polypeptides, polynucleotides and methods of use for modified transcriptional activators allow regulation of gene expression.

6 Claims, 9 Drawing Sheets

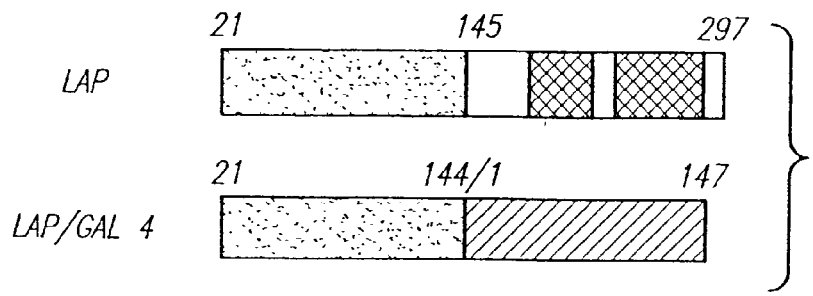
FIG. 4A
FIG. 4B
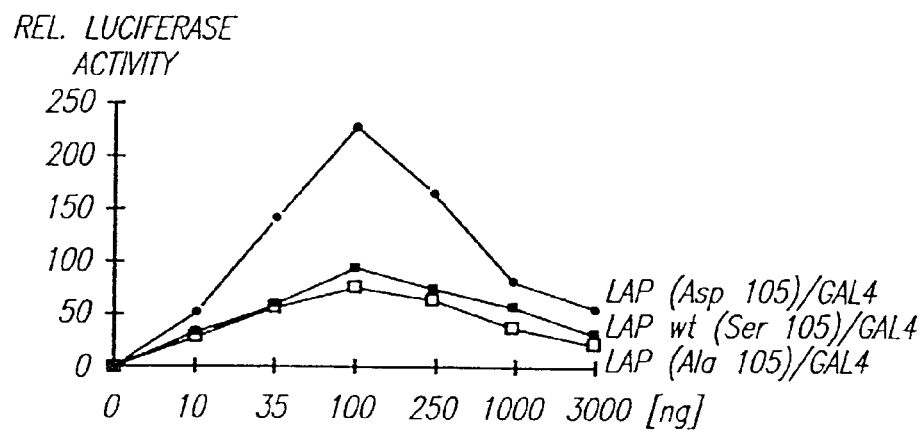
FIG. 4C
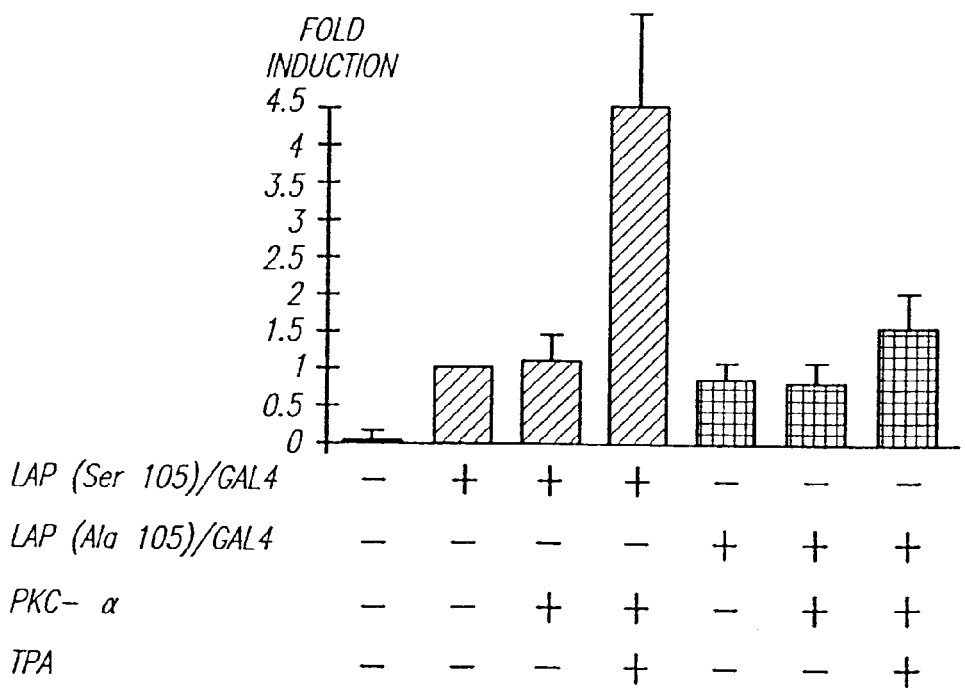

FIG. 5

```
   1 AGGGGCCCCGGCGTGACGCAGCCCGTTGCCAGGCGCGGCCGCCTTATAAACCTCCGCTCGGCCGCCGCCGAGCCGAGTCCGCTCGGCGACGCGGAGCCCGCGGCCCC
 121 GCGTTCATGCACCCGCTGCTGGCCTGGGACGCAGCCATGCGCCGCCTTTAGACCTCTACTACGAAGTGCCAACTTCTACTACGAGCCCGACTGCTGCTACGGGGCC
               M  R  L  L  A  W  D  A  A  C  L  P  P  P  A  A  F  R  P  M  E  V  A  N  F  Y  Y  E  P  D  C  L  A  Y  G  A  38
 241 AAGGGCGCCCGGCCCCGGCGCGCCCCCGAGCGCCCATCGGCCGAGAGCCCGAGCCCGCGGCCGAGCCGGCCGCTCGGCCCGCGGCGCCTCGAGCCGTTCAGCGACTTCGC
           K  A  A  R  A  A  P  R  A  A  P  A  A  E  P  A  I  G  E  H  E  R  A  I  D  F  S  P  Y  L  E  P  L  A  P  A  A  D  F  A  78
 361 GCGCCCGGCCCCGGCGCCACCGACTTCCTTTCGCCGACCTCTTCGCCGACGACTACGGCGCCAAGCCGTCCAAGAAGCCGTCCGACTACGGCTACGTGAGCCTGGGCAGGGCTGCCAAG
           A  P  A  P  A  H  H  D  F  L  S  D  L  F  A  D  D  Y  G  A  K  P  S  K  K  P  S  D  Y  G  Y  V  S  L  G  R  A  G  A  K  118
 481 GCCGCACCGGCCCCGCTTCCCGCCCCGCCCCCGCCGGCAGCTCAAGGCCGAGCCGGGCTTCGAACCCGCCGACTGCAAGCGCGCCGACGACGCCGCCATGGCCGCCGGCTTCCCG
           A  A  P  P  A  C  F  P  P  P  P  P  A  A  L  K  A  E  P  G  F  E  P  A  D  C  K  R  A  D  D  A  P  A  M  A  A  G  F  P  158
 601 TTTCGCCCTGCGCGCCTTCCTGGGCTACCTGGGCTACCAGGCGACGCCCAGCGGCAGCCTGTCGTCCTCGTCGCTCTCCACGTCGCAGCCTCCACGGCCACCGGGCACGTTCCCGAGCCCCGACGCCGCG
           F  A  L  R  A  Y  L  G  Y  Q  A  T  P  S  G  S  L  S  T  S  S  S  P  P  G  T  P  S  P  A  D  A  K  A  A  198
 721 CCCGCCGCCTGCTTCGCCGGGACAAGGCCAAGATGCCAAGACGCCAAGACCGCAACAAGGTGCTGCAGAACGCAGCGAGAACATCGCGGTGCGC
           P  A  A  C  F  A  G  P  P  A  K  A  K  A  K  K  A  K  A  V  D  K  L  S  D  E  Y  K  M  R  R  E  R  N  N  I  A  V  R  238
 841 AAGAGCCGCGACAAGGCCAAGATGCGCAACCTGGAGACGCAAACTGCTGGCCCTGCTCGGGGTCGACCTGCTAGCCCGGGGGCACCGTGGCCTGGGCCCTGCCCCTGC
           K  S  R  D  K  A  K  M  R  N  L  E  T  Q  H  K  V  L  E  L  T  A  E  N  E  R  L  Q  K  K  V  E  Q  L  S  R  E  L  S  T  278
 961 CTGCGGGAACTTGTTCAAGCAGCTGCCCGAGCCGCTGCTGGCCTCGGCGGGTCACTGCTAGCCCGGGCGCGGGTGCGTGGGGGTGGGCTCCCGGGTTCGGGAC
           L  R  N  L  F  K  Q  L  P  E  P  L  L  A  S  A  G  H  C  297
1081 GCGCTCCGTCCCCGGCGGGGCTCCGGCTGCGTGCTTGCTGCACGCCGAGGGGCACACGTGGGCACTGCCCTGAGTTCAGCCGGTTTCGGGGAC
1201 TTGATGCAATCCGGATCAAACTGGCTGGCTGCTGAGCGTGGACGACGTGACGCAACACGTCAACATTTTTTGTATATAAAAGTTCTATTCTATGAGAATGTTCCTGCGGGGTTGTTGC
1321 TGTTGATGTGTTTTCCTTTCGACGATTAAAGTGAAGACATTTGTTTTTTGTGTGAATGTTAAAAACCTTTTGGGGCAGTAGTTGGCTTTGAAAAAAATTTTTTCTTCCTCCTGAC
1441 CTTTTCGTTTCGAGCATTAAAGTGAAGACATTTGTTTTTTGTGTGAATGTTAAAAACCTTTTGGGGCAGTAGTTGGCTTTGAAAAAAATTTTTTCTTCCTCCTGAC
1561 TTTGGATTTATGCGAGATTTGTTTTTTGTCGTGTGTAGGGGCTGCGGGTTATTTTGGTGTGTGGTGTGGTGGGCAGTGCCAGGTCAGGAATTC
1681 CAGATGGGATGCCAGCCCCTCCCCCAGGAGAGAGGGGCAGAGTGCCGGTCAGGAATTC  1739
```

REGULATION OF TRANSCRIPTION FACTOR, NF-IL6/LAP

This application is a continuation of U.S. Ser. No. 09/080,633 filed May 18, 1998 now abandoned; which is a divisional of U.S. Ser. No. 08/436,874 filed May 8, 1995 (now U.S. Pat. No. 5,874,209); which is a divisional of U.S. Ser. No. 08/096,177 filed Jul. 20, 1993 (abandoned). The disclosure of the prior applications is considered part of and is incorporated by reference in the disclosure of this application.

This invention was made with Government support under grant Nos. CA 50528 and HL 35018, awarded by the National Institutes of Health. The Government has certain rights in this invention.

BACKGROUND OF THE INVENTION

1. Field of the Invention

This invention relates to the field of regulation of expression of genes and, specifically, to the regulation and activation of genes by the transcription factor, NF-IL6/LAP.

2. Description of Related Art

Many eukaryotic genes are regulated in an inducible, cell type-specific or constitutive manner. There are different types of structural elements which are involved in the regulation of gene expression. There are cis-acting elements, located in the proximity of, or within, genes which serve to bind sequence-specific DNA binding proteins or trans-acting factors. The binding of proteins to DNA is responsible for the initiation, maintenance, or down-regulation of transcription of genes.

The cis-acting elements which control genes are called promoters, enhancers or silencers. Promoters are positioned next to the start site of transcription and function in an orientation-dependent manner, while enhancer and silencer elements, which modulate the activity of promoters, are flexible with respect to their orientation and distance to the start site of transcription.

Extracellular signals modulate the activity of many types of transcription factors. One important group of signal-regulated transcription factors are the BZip proteins, named because of their conserved basic (B) and leucine zipper (Zip) domains that are required for DNA binding and dimerization, respectively. Some well-studied examples of this family of transcription activator proteins include the AP-1/jun/fos family of transcription factors and CREB/ATF proteins which bind to the TPA (12-O-tetradecanoylphorbol-13-acetate) response element and cyclic AMP (cAMP) response element (CRE), respectively. Regulation by BZip proteins can involve a variety of complex mechanisms—transcriptional, temporal and post-translational—that affect the level and the repertoire of the factors expressed in a given cell, as well as their DNA binding and transcriptional activation functions.

NF-IL6/LAP (nuclear factor-interleukin 6/lymphokine activating protein) is a member of the bZIP family of transcriptional activators. NF-IL6/LAP protein is highly enriched in liver nuclei, where it has been implicated as a major regulator of acute-phase response. It is induced by interleukin-6 (IL-6) and other inflammatory mediators. NF-IL6/LAP is also involved in the activation of the IL-6 promoter in response to IL-1 and bacterial lipopolysaccharide (LPS). NF-IL6/LAP is involved in the induction of several cytokine genes including interleukin 6 (IL-6), interleukin 8 (IL-8), granulocyte-colony stimulating factor (G-CSF) and tumor necrosis factor alpha (TNF-α). These genes contain cis-acting elements which include a NF-IL6/LAP recognition sequence.

For many years, various drugs have been tested for their ability to alter the expression of genes or the translation of their messages into protein products. One problem with existing drug therapy is that it tends to act indiscriminately and affect healthy cells as well as neoplastic cells. This is a major problem with many forms of chemotherapy where there are severe side effect primarily due to the action of toxic drugs on healthy cells.

In view of the foregoing, there is a need to identify specific targets in the abnormal cell which are associated with the overexpression of genes whose expression products are implicated in cell proliferatve disorders, in order to decrease potential negative effect on healthy cells. The present invention provides such a target.

SUMMARY OF THE INVENTION

The present invention is founded on the unexpected discovery of a site-specific post-translational modification of NF-IL6/LAP that enhances its ability to activate various target genes, such as cytokine genes. The modification is phosphorylation of NF-IL6/LAP at serine residue number 105. The invention provides a polypeptide having transactivation activity and having the amino acid sequence of NF-IL6/LAP with an amino acid substitution at residues 105.

The invention provides a method of treating an immunopathological or cell proliferative disorder associated with NF-IL6/LAP by administering to a subject with the disorder, a therapeutically effective amount of a reagent which modulates NF-IL6/LAP activity.

The invention also provides a synthetic peptide comprising the region on NF-IL6/LAP which corresponds to amino acids from about position 75 to about position 125 and includes a serine residue at position 105 which is the phosphorylation site. In addition, the invention provides peptides where the serine at residue 105 is substituted with a non-phosphorylatable analog (e.g., alanine). The peptides are useful as a competitive inhibitor or a pseudosubstrate for the kinase that phosphorylates naturally occurring NF-L6/LAP in situations where it is desirable to decrease the amount of NF-IL6/LAP activation.

BRIEF DESCRIPTION OF THE DRAWINGS

FIG. 4A shows a schematic drawing of the transactivation domain of NF-IL6/LAP(aa 21-144) ligated to the N-terminus of the yeast GAL4 DNA-binding domain (aa 1-147) to generate the chimeric activator LAP/GAL4. FIG. 4B shows Luciferase activity for cells transfected with the GAL4-responsive reporter 5×GAL4-LUC and pSV40-LAP (Ser105)/GAL4, pSV40-LAP(ALA105)/GAL4 or pSV40-LAP(Asp105)/GAL4 expression vectors. FIG. 4C is the same as 48, however, the plasmid pCDM8-PKCα was also transfected.

FIG. 5 shows the nucleotide (SEQUENCE ID NO:3) and amino acid (SEQUENCE ID NO:4) sequences of NF-IL6/LAP. Amino Acid Sequences 75 to 125 are underlined.

DETAILED DESCRIPTION OF THE INVENTION

Figure 1A:
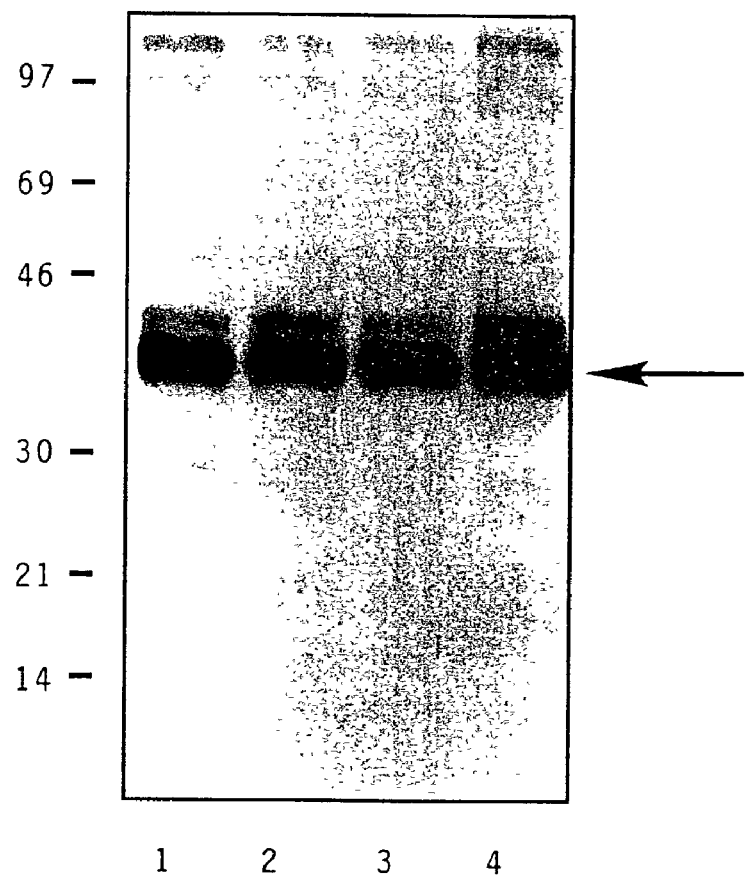
FIG. 1A shows an immunoprecipitation of HepG2 cells transfected with CMV-LAP and cotransfected with either pUC19, pCDM8-0, or pCDM-PKCα, treated with TPA, labelled with $^{32}$P-NF-IL6/LAP; 1B shows Western blotting of HepG2 cells stimulated with TPA; 1C shows tryptic phosphopeptide maps of in vivo labelled NF-IL6/LAP.

The present invention is based on the discovery of the specific site within the transcription factor NF-IL6/LAP activation domain, which, when phosphorylated, augments the ability of NF-IL6/LAP to activate genes containing a NF-IL6/LAP recognition site. Since NF-IL6/LAP is a transactivator protein which binds at a specific site on a gene, regulation of NF-IL6/LAP activation may be important in normal gene expression, cellular growth control and inflammation. The discovery of the specific phosphorylation site at serine residue 105, provides a means for controlling gene expression of those genes which contain a NF-IL6/LAP recognition site.

The invention provides a polypeptide with the amino acid sequence of wild-type NF-IL6/LAP, however, the amino acid at position 105 can be substituted with an amino acid which either enhances transactivating activity or decreases transactivating activity. Preferably, when it is desirable to enhance the activity, a negatively charged amino acid such as aspartic acid or glutamic acid is substituted. When it is desirable to decrease NF-IL6/LAP activity, a neutral amino acid is substituted. Preferably, the neutral amino acid is alanine. Other amino acids which increase or decrease the transactivating activity of wild-type NF-IL6/LAP can be substituted for serine at position 105. Other amino acids which may be substituted include synthetic amino acids which are chemically produced or modified and are capable of altering NF-IL6/LAP transactivating activity.

Minor modifications of the primary amino acid sequence of the polypeptides of the invention may result in polypeptides which have substantially equivalent activity as compared to the specific polypeptides described herein. Such modifications may be deliberate, as by site-directed mutagenesis, or may be spontaneous. All of the peptides produced by these modifications are included herein as long as the biological activity of the polypeptides still exists. For example, the polypeptide still acts as a competitive inhibitor for the natural NF-IL6/LAP phosphorylation site (Ser105), provides a less well recognized phosphorylation site (Ala105) and provides a site which increases transactivation (Asp105). Further, deletion of one or more amino acids can also result in a modification of the structure of the resultant molecule without significantly altering its activity. This can lead to the development of a smaller active molecule which would have broader utility. For example, one can remove amino or carboxy terminal amino acids which may not be required for biological activity.

The NF-IL6/LAP polypeptides of the invention also include conservative variations of the polypeptide sequence. In addition to the discrete substitution at the serine 105 phosphorylation site described above, the invention embraces conservative variations in the remaining amino acid sequence of the polypeptides of the invention. The term "conservative variation" as used herein denotes the replacement of an amino acid residue by another, biologically similar residue. Examples of conservative variations include the substitution of one hydrophobic residue such as isoleucine, valine, leucine or methionine for another, or the substitution of one polar residue for another, such as the substitution of arginine for lysine, glutamic for aspartic acids, or glutamine for asparagine, and the like. The term "conservative variation" also includes the use of a substituted amino acid in place of an unsubstituted parent amino acid provided that antibodies raised to the substituted polypeptide also immuno-react with the unsubstituted polypeptide.

The invention also provides a synthetic peptide with the amino acid sequence of Sequence ID No. 1, and conservative variations thereof. This sequence represents amino acids 75-125 of NF-IL6/LAP polypeptide and contains a serine at position 105 which is the site for phosphorylation and subsequent activation of NF-IL6/LAP (Akira, et al., *EMBO J.*, 6:1897, 1990; Descombes, et al., *Genes & Dev.*, 4:1541, 1990; Poli, et al., *Cell*, 63:643, 1990). As used herein, the term "synthetic peptide" denotes a peptide which does not comprise an entire naturally occurring protein molecule. The peptide is "synthetic" in that it may be produced by human intervention using such techniques as chemical synthesis, recombinant genetic techniques, or fragmentation of whole antigen or the like.

The invention also includes a peptide which has the sequence of Sequence ID No. 1 where the serine at position 105 of natural NF-IL-6/LAP is modified. For example, one modification is the substitution of serine with alanine, thereby rendering the peptide hypophosphorylated. The invention also includes a peptide which has the sequence of Sequence ID No. 1 where the serine at position 105 of natural NF-IL-6/LAP is substituted with a negatively charged amino acid, thereby enhancing the transactivation activity. Examples of such negatively charged amino acids which enhance the transactivation activity of NF-IL6/LAP include aspartic acid and glutamic acid.

Peptides of the invention can be synthesized by such commonly used methods as t-BOC or FMOC protection of alpha-amino groups. Both methods involve stepwise syntheses whereby a single amino acid is added at each step starting from the C terminus of the peptide (See, Coligan, et al., *Current Protocols in Immunology*, Wiley Interscience, 1991, Unit 9). Peptides of the invention can also be synthesized by the well known solid phase peptide synthesis methods described Merrifield, *J. Am. Chem. Soc.*, 85:2149, 1962), and Stewart and Young, *Solid Phase Peptides Synthesis*, (Freeman, San Francisco, 1969, pp. 27-62), using a copoly(styrene-divinylbenzene) containing 0.1-1.0 mMol amines/g polymer. On completion of chemical synthesis, the peptides can be deprotected and cleaved from the polymer by treatment with liquid HF-10% anisole for about ¼-1 hours at 0° C. After evaporation of the reagents, the peptides are extracted from the polymer with 1% acetic acid solution which is then lyophilized to yield the crude material. This can normally be purified by such techniques as gel filtration on Sephadex G-15 using 5% acetic acid as a solvent Lyophilization of appropriate fractions of the column will yield the homogeneous peptide or peptide derivatives, which can then be characterized by such standard techniques as amino acid analysis, thin layer chromatography, high performance liquid chromatography, ultraviolet absorption spectroscopy, molar rotation, solubility, and quantitated by the solid phase Edman degradation.

The invention also provides polynucleotides which encode the NF-IL6/LAP polypeptides of the invention and the synthetic peptides of Sequence ID No.1 and the modifications described. As used herein, "polynucleotide" refers to a polymer of deoxyribonucleotides or ribonucleotides, in the form of a separate fragment or as a component of a larger construct. DNA encoding the polypeptide of the invention can be assembled from cDNA fragments or from oligonucleotides which provide a synthetic gene which is capable of being expressed in a recombinant transcriptional unit. Polynucleotide sequences of the invention include DNA, RNA and cDNA sequences.

DNA sequences of the invention can be obtained by several methods. For example, the DNA can be isolated using hybridization procedures which are well known in the art. These include, but are not limited to: 1) hybridization of probes to genomic or cDNA libraries to detect shared nucleotide sequences; 2) antibody screening of expression libraries to detect shared structural features and 3) synthesis by the polymerase chain reaction (PCR).

Hybridization procedures are useful for the screening of recombinant clones by using labeled mixed synthetic oligonucleotide probes where each probe is potentially the complete complement of a specific DNA sequence in the hybridization sample which includes a heterogeneous mixture of denatured double-stranded DNA. For such screening, hybridization is preferably performed on either single-stranded DNA or denatured double-stranded DNA. Hybridization is particularly useful in the detection of cDNA clones derived from sources where an extremely low amount of mRNA sequences relating to the polypeptide of interest are present. In other words, by using stringent hybridization conditions directed to avoid non-specific binding, it is possible, for example, to allow the autoradiographic visualization of a specific cDNA clone by the hybridization of the target DNA to that single probe in the mixture which is its complete complement (Wallace, et al., *Nucleic Acid Research*, 9:879, 1981).

The development of specific DNA sequences encoding the NF-IL6/LAP polypeptides of the invention can also be obtained by: 1) isolation of double-stranded DNA sequences from the genomic DNA; 2) chemical manufacture of a DNA sequence to provide the necessary codons for the polypeptide of interest; and 3) in vitro synthesis of a double-stranded DNA sequence by reverse transcription of mRNA isolated from a eukaryotic donor cell. In the latter case, a double-stranded DNA complement of mRNA is eventually formed which is generally referred to as cDNA. Of these three methods for developing specific DNA sequences for use in recombinant procedures, the isolation of genomic DNA isolates is the least common. This is especially true when it is desirable to obtain the microbial expression of mammalian polypeptides due to the presence of introns.

The synthesis of DNA sequences is frequently the method of choice when the entire sequence of amino acid residues of the desired polypeptide product is known. When the entire sequence of amino acid residues of the desired polypeptide is not known, the direct synthesis of DNA sequences is not possible and the method of choice is the synthesis of cDNA sequences.

Among the standard procedures for isolating cDNA sequences of interest is the formation of plasmid- or phage carrying cDNA libraries which are derived from reverse transcription of mRNA which is abundant in donor cells that have a high level of genetic expression. When used in combination with polymerase chain reaction technology, even rare expression products can be cloned. In those cases where significant portions of the amino acid sequence of the polypeptide are known, the production of labeled single or double-stranded DNA or RNA probe sequences duplicating a sequence putatively present in the target cDNA may be employed in DNA/DNA hybridization procedures which are carried out on cloned copies of the cDNA which have been denatured into a single-stranded form (Jay et al., *Nucl. Acid Res.* 11:2325, 1983).

A cDNA expression library, such as lambda gt11, can be screened indirectly for NF-IL6/LAP polypeptides having at least one epitope, using antibodies specific for NF-IL6/LAP. Such antibodies can be either polyclonally or monoclonally derived and used to detect expression product indicative of the presence of NF-IL6/LAP cDNA.

A polynucleotide sequence can be deduced from the genetic code, however, the degeneracy of the code must be taken into account Polynucleotides of the invention include sequences which are degenerate as a result of the genetic code. The polynucleotides of the invention include sequences that are degenerate as a result of the genetic code. There are 20 natural amino acids, most of which are specified by more than one codon. Therefore, as long as the amino acid sequence of NF-IL6/LAP results in a functional polypeptide (at least, in the case of the sense polynucleotide strand), all degenerate nucleotide sequences are included in the invention.

Polynucleotide sequences encoding the polypeptides or synthetic peptides (Sequence ID No. 1) of the invention can be expressed in either prokaryotes or eukaryotes. Hosts can include microbial, yeast, insect and mammalian organisms. Methods of expressing DNA sequences having eukaryotic or viral sequences in prokaryotes are well known in the art Biologically functional viral and plasmid DNA vectors capable of expression and replication in a host are known in the art. Such vectors are used to incorporate DNA sequences of the invention.

DNA sequences encoding the polypeptides can be expressed in vitro by DNA transfer into a suitable host cell. "Host cells" are cells in which a vector can be propagated and its DNA expressed. The term also includes any progeny of the subject host cell. It is understood that all progeny may not be identical to the parental cell since there may be mutations that occur during replication. However, such progeny are included when the term "host cell" is used. Methods of stable transfer, in other words when the foreign DNA is continuously maintained in the host, are known in the art.

In the present invention, the NF-IL6/LAP polynucleotide sequences may be inserted into a recombinant expression vector. The term "recombinant expression vector" refers to a plasmid, virus or other vehicle known in the art that has been manipulated by insertion or incorporation of the genetic sequences. Such expression vectors contain a promoter sequence which facilitates the efficient transcription of the inserted genetic sequence of the host. The expression vector typically contains an origin of replication, a promoter, as well as specific genes which allow phenotypic selection of the transformed cells. Vectors suitable for use in the present invention include, but are not limited to the T7-based expression vector for expression in bacteria (Rosenberg et al., *Gene* 56:125, 1987), the pMSXND expression vector for expression in mammalian cells (Lee and Nathans, *J. Biol.*

*Chem.* 263:3521, 1988) and baculovirus-derived vectors for expression in insect cells. The DNA segment can be present in the vector operably linked to regulatory elements, for example, a promoter (e.g., 17, metallothionein 1, or polyhedrin promoters).

The vector may include a phenotypically selectable marker to identify host cells which contain the expression vector. Examples of markers typically used in prokaryotic expression vectors include antibiotic resistance genes for ampicillin (β-lactamases), tetracycline and chloramphenicol (chloramphenicol acetyl-transferase). Examples of such markers typically used in mammalian expression vectors include the gene for adenosine deaminase (ADA), aminoglycoside phosphotransferase (neo, G418), dihydrofolate reductase (DHFR), hygromycin-B-phosphotransferase (HPH), thymidine kinase (TK), and xanthine guanine phosphoribosyltransferse (XGPRT, gpt).

Transformation of a host cell with recombinant DNA may be carried out by conventional techniques which are well known to those skilled in the art. Where the host is prokaryotic, such as *E. coli*, competent cells which are capable of DNA uptake can be prepared from cells harvested after exponential growth phase and subsequently treated by the $CaCl_2$ method by procedures well known in the art. Alternatively, $MgCl_2$ or $RbCl$ can be used. Transformation can also be performed after forming a protoplast of the host cell or by electroporation.

When the host is a eukaryote, such methods of transfection of DNA as calcium phosphate co-precipitates, conventional mechanical procedures such as microinjection, electroporation, insertion of a plasmid encased in liposomes, or virus vectors may be used. Eukaryotic cells can also be cotransformed with DNA sequences encoding the polypeptides of the invention, and a second foreign DNA molecule encoding a selectable phenotype, such as the herpes simplex thymidine kinase gene. Another method is to use a eukaryotic viral vector, such as simian virus 40 (SV40) or bovine papilloma virus, to transiently infect or transform eukaryotic cells and express the protein. (*Eukaryotic Viral Vectors*, Cold Spring Harbor Laboratory, Gluzman ed., 1982). Examples of mammalian host cells include COS, BHK, 293, and CHO cells.

Isolation and purification of host cell expressed polypeptide, or fragments thereof, provided by the invention, may be carried out by conventional means including preparative chromatography and immunological separations involving monoclonal or polyclonal antibodies.

In addition, ribozyme nucleotide sequences for NF-IL6/LAP are included in the invention. Ribozymes are RNA molecules possessing the ability to specifically cleave other single-stranded RNA in a manner analogous to DNA restriction endonucleases. Through the modification of nucleotide sequences which encode these RNAs, it is possible to engineer molecules that recognize specific nucleotide sequences in an RNA molecule and cleave it (Cech, *J. Amer. Med.-Assn.*, 260:3030, 1988). A major advantage of this approach is that, because they are sequence-specific, only mRNAs with particular sequences are inactivated. For example, ribozymes could be directed to the region surrounding and including the phosphorylation site of NF-IL6/LAP.

There are two basic types of ribozymes namely, *tetrahymena*-type (Hasselhoff, *Nature*, 334:585, 1988) and "hammerhead"-type. *Tetrahymena*-type ribozymes recognize sequences which are four bases in length, while "hammerhead"-type ribozymes recognize base sequences 11-18 bases in length. The longer the recognition sequence, the greater the likelihood that that sequence will occur exclusively in the target mRNA species. Consequently, hammerhead-type ribozymes are preferable to *tetrahymena*-type ribozymes for inactivating a specific mRNA species and 18-based recognition sequences are preferable to shorter recognition sequences.

Antibodies provided in the present invention are immunoreactive or bind to the polypeptides or peptides of the invention. Antibody which consists essentially of pooled monoclonal antibodies with different epitopic specificities, as well as distinct monoclonal antibody preparations are provided. Monoclonal antibodies are made from antigen containing fragments of the protein by methods well known in the art (Kohler, et al., *Nature*, 256:495, 1975; *Current Protocols in Molecular Biology*, Ausubel, et al., ed., 1989).

Antibodies which bind to the NF-IL6/LAP polypeptides of the invention can be prepared using an intact polypeptide or fragments containing small peptides of interest as the immunizing antigen. The polypeptide or a peptide, such as Sequence ID No. 1, used to immunize an animal can be derived from translated cDNA or chemical synthesis and is purified and conjugated to a carrier protein, if desired. Such commonly used carriers which are chemically coupled to the peptide include keyhole limpet hemocyanin (KLH), thyroglobulin, bovine serum albumin (BSA), and tetanus toxoid. The coupled peptide is then used to immunize the animal (e.g., a mouse, a rat, or a rabbit).

If desired, polyclonal antibodies can be further purified, for example, by binding to and elution from a matrix to which the polypeptide or a peptide to which the antibodies were raised is bound. Those of skill in the art will know of various techniques common in the immunology arts for purification and/or concentration of polyclonal antibodies, as well as monoclonal antibodies (See for example, Coligan, et al., Unit 9, *Current Protocols in Immunology*, Wiley Interscience, 1991, incorporated by reference).

The term "antibody" as used in this invention includes intact molecules as well as fragments thereof, such as Fab, $F(ab')_2$, and Fv which are capable of binding the epitopic determinant. These antibody fragments retain some ability to selectively bind with its antigen or receptor and are defined as follows:

(1) Fab, the fragment which contains a monovalent antigen-binding fragment of an antibody molecule can be produced by digestion of whole antibody with the enzyme papain to yield an intact light chain and a portion of one heavy chain;

(2) Fab', the fragment of an antibody molecule can be obtained by treating whole antibody with pepsin, followed by reduction, to yield an intact light chain and a portion of the heavy chain; two Fab' fragments are obtained per antibody molecule;

(3) $(Fab')_2$, the fragment of the antibody that can be obtained by treating whole antibody with the enzyme pepsin without subsequent reduction; $F(ab')_2$ is a dimer of two Fab' fragments held together by two disulfide bonds;

(4) Fv, defined as a genetically engineered fragment containing the variable region of the light chain and the variable region of the heavy chain expressed as two chains; and (5) Single chain antibody ("SCA"), defined as a genetically engineered molecule containing the variable region of the light chain, the variable region of the heavy chain, linked by a suitable polypeptide linker as a genetically fused single chain molecule.

Methods of making these fragments are known in the art. (See for example, Harlow and Lane, *Antibodies: A Labora-*

*tory Manual*, Cold Spring Harbor Laboratory, New York (1988), incorporated herein by reference).

As used in this invention, the term "epitope" means any antigenic determinant on an antigen to which the paratope of an antibody binds. Epitopic determinants usually consist of chemically active surface groupings of molecules such as amino acids or sugar side chains and usually have specific three dimensional structural characteristics, as well as specific charge characteristics.

It is also possible to use the anti-idiotype technology to produce monoclonal antibodies which mimic an epitope. For example, an anti-idiotypic monoclonal antibody made to a first monoclonal antibody will have a binding domain in the hypervariable region which is the "image" of the epitope bound by the first monoclonal antibody. Thus, in the present invention, an anti-idiotype antibody produced from an antibody which binds to the NF-IL6/LAP polynucleotides or a synthetic peptide of Sequence ID No.1, can act as a competitive inhibitor for site on NF-IL6/LAP which is required for phosphorylation and subsequent activation of genes containing a NF-IL6/LAP recognition site, thereby preventing NF-IL6/LAP from activating specific genes.

The NF-IL6/LAP transactivator protein of the invention is useful in a screening method to identify compounds or compositions which affect the activity of the protein. Thus, in one embodiment, the invention provides a method for identifying a composition which affects NF-IL6/LAP comprising incubating the components, which include the composition to be tested and the NF-IL6/LAP, under conditions sufficient to allow the components to interact, then subsequently measuring the effect the composition has on transactivation activity. The observed effect on NF-IL6/LAP may be either inhibitory or stimulatory. For example, the increase or decrease of transactivation activity can be measured by adding a radioactive compound to the mixture of components, such as $^{32}$P-ATP, and observing radioactive incorporation at serine 105 of NF-IL6/LAP or a peptide of the invention which includes serine 105 (Sequence ID No.1), to determine whether the compound inhibits or stimulates transactivation activity.

This method is also useful for measuring the effect of a composition on NF-IL6/LAP polypeptides which include a substitution at serine 105. Alternatively, other labels may be used to determine the effect of a composition on NF-IL6/LAP. For example, a radioisotope, a fluorescent compound, a bioluminescent compound, a chemiluminescent compound, a metal chelator or an enzyme could be used. Those of ordinary skill in the art will know of other suitable labels or will be able to ascertain such, using routine experimentation.

The invention also provides a method of treating an immunopathological disorder associated with NF-IL6/LAP comprising administering to a subject with the disorder, a therapeutically effective amount of reagent which modulates NF-IL6/LAP activity. The term "immunopathological disorder" refers to any disease which involves the immune response or immunity in general.

The method of the invention could equally be used for treating a cell proliferative disorder associated with NF-IL6/LAP as described above for an immunopathological disorder. The term "therapeutically effective" means that the amount of polypeptide, peptide, polynucleotide, or monoclonal antibody for example, which is used, is of sufficient quantity to ameliorate the NF-IL6/LAP associated disorder. The term "cell-proliferative disorder" denotes malignant as well as non-malignant cell populations which morphologically often appear to differ from the surrounding tissue. For example, the method may be useful in treating malignancies of the various organ systems, such as, for example, lung, breast, lymphoid, gastrointestinal, and genito-urinary tract as well as adenocarcinomas which include malignancies such as most colon cancers, renal-cell carcinoma, prostate cancer, non-small cell carcinoma of the lung, cancer of the small intestine, and cancer of the esophagus.

The method is also useful in treating non-malignant or immunological-related cell-proliferatve diseases such as psoriasis, pemphigus vulgaris, Behcet's syndrome, acute respiratory distress syndrome (ARDS), ischemic heart disease, post-dialysis syndrome, leukemia, rheumatoid arthritis, acquired immune deficiency syndrome, vasculitis, lipid histiocytosis, septic shock and inflammation in general. Essentially, any disorder which is etiologically linked to NF-IL6/LAP would be considered susceptible to treatment.

Treatment of an immunopathological disorder according to the method of the invention includes administration of a reagent which modulates NF-IL6/LAP activity. The term "modulate" envisions the suppression of NF-IL6/LAP activation when it is hyperphosphorylated, or augmentation of NF-IL6/LAP activation when it is hypophosphorylated. When an immunopathological or cell proliferative disorder is associated with hyperphosphorylation, such suppressive reagents as the peptide of Sequence ID No. 1 may be used as a competitive inhibitor of the natural NF-IL6/LAP in a cell. For example, NF-IL6/LAP(Ser105) or (Asp105) peptides can be introduced to a cell and would compete for phosphorylation with a NF-IL6/LAP kinase. These peptides would be unable to act as transcription factors. In addition, an NF-IL6/LAP binding antibody or an anti-idiotype antibody which binds to a monoclonal antibody which binds a peptide of the invention may also be used in the therapeutic method of the invention. When an immunopathological disorder is associated with hypophosphorylation of NF-IL6/LAP and corresponding low levels of expression from genes which contain an NF-IL6/LAP recognition site, a polypeptide of the invention which contains a negatively charged amino acid at position 105 would be useful in the method of the invention.

Genes which contain an NF-IL6/LAP recognition site include cytokine genes. Therefore, the method of the invention is useful for treating immunopathological disorders associated with expression of cytokine genes. Examples of these genes include interleukin 6 (IL-6), interleukin 8 (IL-8), granulocyte-colony stimulating factor (G-CSF) and tumor necrosis factor alpha (TNF).

The antibodies of the invention can be administered parenterally by injection or by gradual infusion over time. The monoclonal antibodies of the invention can be administered intravenously, intraperitoneally, intramuscularly, subcutaneously, intracavity, or transdermally.

The peptides of the invention can be administered by methods described for administration of the monoclonal antibodies. Preferred methods for delivery of the peptide include orally, by encapsulation in microspheres or proteinoids, by aerosol delivery to the lungs, or transdermally by iontophoresis or transdermal electroporation. Other methods of administration will be known to those skilled in the art.

Preparations for parenteral administration of a peptide or an antibody of the invention include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media Parenteral vehicles include sodium chloride solution, Ringer's dextrose, dextrose and sodium chloride, lactated Ringer's, or fixed oils. Intravenous vehicles include fluid and nutrient replenishers, electrolyte replenishers (such as those based on Ringer's dextrose), and the like. Preservatives and other additives may also be present such as, for example, antimicrobials, antioxidants, chelating agents, and inert gases and the like.

Polynucleotide sequences can be therapeutically administered by various techniques known to those of skill in the art. Such therapy would achieve its therapeutic effect by introduction of the NF-IL6/LAP polynucleotide, into cells of animals having the proliferative disorder. Delivery of NF-IL6/LAP polynucleotide can be achieved using a recombinant expression vector such as a chimeric virus or a colloidal dispersion system. Especially preferred for therapeutic delivery of nucleotide sequences is the use of targeted liposomes.

Various viral vectors which can be utilized for gene therapy as taught herein include adenovirus, herpes virus, vaccinia, or, preferably, an RNA virus such as a retrovirus. Preferably, the retroviral vector is a derivative of a murine or avian retrovirus. Examples of retroviral vectors in which a single foreign gene can be inserted include, but are not limited to: Moloney murine leukemia virus (MoMuLV), Harvey murine sarcoma virus (HaMuSV), murine mammary tumor virus (MuMTV), and Rous Sarcoma Virus (RSV). A number of additional retroviral vectors can incorporate multiple genes. All of these vectors can transfer or incorporate a gene for a selectable marker so that transduced cells can be identified and generated. By inserting a NF-IL6/LAP sequence into the viral vector, along with another gene which encodes the ligand for a receptor on a specific target cell, for example, the vector is now target specific. Retroviral vectors can be made target specific by inserting, for example, a polynucleotide encoding a sugar, a glycolipid, or a protein. Preferred targeting is accomplished by using an antibody to target the retroviral vector. Those of skill in the art will know of, or can readily ascertain without undue experimentation, specific polynucleotide sequences which can be inserted into the retroviral genome to allow target specific delivery of the retroviral vector containing the NF-IL6/LAP polynucleotide.

Since recombinant retroviruses are defective, they require assistance in order to produce infectious vector particles. This assistance can be provided, for example, by using helper cell lines that contain plasmids encoding all of the structural genes of the retrovirus under the control of regulatory sequences within the LTR. These plasmids are missing a nucleotide sequence which enables the packaging mechanism to recognize an RNA transcript for encapsitation. Helper cell lines which have deletions of the packaging signal include but are not limited to Ψ2, PA317 and PA12, for example. These cell lines produce empty virions, since no genome is packaged. If a retroviral vector is introduced into such cells in which the packaging signal is intact, but the structural genes are replaced by other genes of interest, the vector can be packaged and vector virion produced. The vector virions produced by this method can then be used to infect a tissue cell line, such as NIH 3T3 cells, to produce large quantities of chimeric retroviral virions.

Another targeted delivery system for NF-IL6/LAP polynucleotides is a colloidal dispersion system. Colloidal dispersion systems include macromolecule complexes, nanocapsules, microspheres, beads, and lipid-based systems including oil-in-water emulsions, micelles, mixed micelles, and liposomes. The preferred colloidal system of this invention is a liposome. Liposomes are artificial membrane vesicles which are useful as delivery vehicles in vitro and in vivo. It has been shown that large unilamellar vesicles (LUV), which range in size from 0.2-4.0 um can encapsulate a substantial percentage of an aqueous buffer containing large macromolecules. RNA, DNA and intact virions can be encapsulated within the aqueous interior and be delivered to cells in a biologically active form (Fraley, et al., *Trends Biochem. Sci.*, 6:77, 1981). In addition to mammalian cells, liposomes have been used for delivery of polynucleotides in plant, yeast and bacterial cells. In order for a liposome to be an efficient gene transfer vehicle, the following characteristics should be present: (1) encapsulation of the genes of interest at high efficiency while not compromising their biological activity; (2) preferential and substantial binding to a target cell in comparison to non-target cells; (3) delivery of the aqueous contents of the vesicle to the target cell cytoplasm at high efficiency, and (4) accurate and effective expression of genetic information (Mannino, et al., *Biotechniques*, 6:682, 1988).

The targeting of liposomes has been classified based on anatomical and mechanistic factors. Anatomical classification is based on the level of selectivity, for example, organ-specific, cell-specific, and organelle-specific. Mechanistic targeting can be distinguished based upon whether it is passive or active. Passive targeting utilizes the natural tendency of liposomes to distribute to cells of the reticuloendothelial system (RES) in organs which contain sinusoidal capillaries. Active targeting, on the other hand, involves alteration of the liposome by coupling the liposome to a specific ligand such as a monoclonal antibody, sugar, glycolipid, or protein, or by changing the composition or size of the liposome in order to achieve targeting to organs and cell types other than the naturally occurring sites of localization.

The discovery of serine 105 as the specific phosphorylation site of NF-IL6/LAP now allows one of skill in the art to identify the specific protein kinase that phosphorylates NF-IL6/LAP. For example, candidate kinases are incubated with NF-IL6/LAP and the incorporation of phosphate at serine 105 is measured to identify NF-IL6/LAP protein kinase.

The following examples are intended to illustrate but not limit the invention. While they are typical of those that might be used, other procedures known to those skilled in the art may alternatively be used.

EXAMPLE 1

Activation of the PKC Pathway Induces Site-Specific Phosphorylation of NF-IL6/LAP Subconfluent cultures of HepG2 cells were transfected using the calcium-phosphate method as described (Descombes, P., et al., *Genes & Dev.*, 4:1541, 1990; Muller, C. R., et al., *Cell*, 61:279, 1990) with pCMV-LAP (wt) (1.0 µg) (Descombes, et al., supra) pGDM8 (3.0 µg) and pGDM8-PKCα (3.0 µg) (James, G., et al., *J. Cell Biol.*, 116:863, 1992). After transfection, cells were kept in medium alone for 40 h and labelled with [$^{32}$P]-orthophosphate (25 mCi/ml) for 4 hr. TPA (100 ng/ml) was added as indicated for the last 20 min. Cells were lysed in RIPA buffer (Radio Immune Precipitation Buffer), NF-IL6/LAP was immunoprecipitated with a specific antibody (Descombes, P., et al., supra, 1990) and separated by SDS-polyacrylamide-gel-electrophoresis as described (Binetruy, B., et al., *Nature*, 351:122, 1991). After blotting onto nitrocellulose, in vivo labelled LAP was digested with trypsin. The digested peptides were eluted off the membrane, spotted on a TLC plate and separated by two-dimensional electrophoresis as described (Boyle, W. J., et al., *Enzymol.*, 201:110, 1991). Nuclear extracts were prepared from HepG2 cells transfected as for $^{32}$P-labeling using described procedures (Descombes, P., et al., supra, 1990) and analyzed by Western blotting using anti-LAP antibodies (Descombes, P., et al., supra, 1990). The antigen-antibody complexes were visualized using the ECL detection system (Amersham). CMV-LAP encodes the form of NF-IL6/LAP which is mostly translated in the liver starting at the second ATG of the NF-IL6/LAP open reading frame (Descombes, P., et al., *Cell*, 67:569, 1991).

Figure 1B:
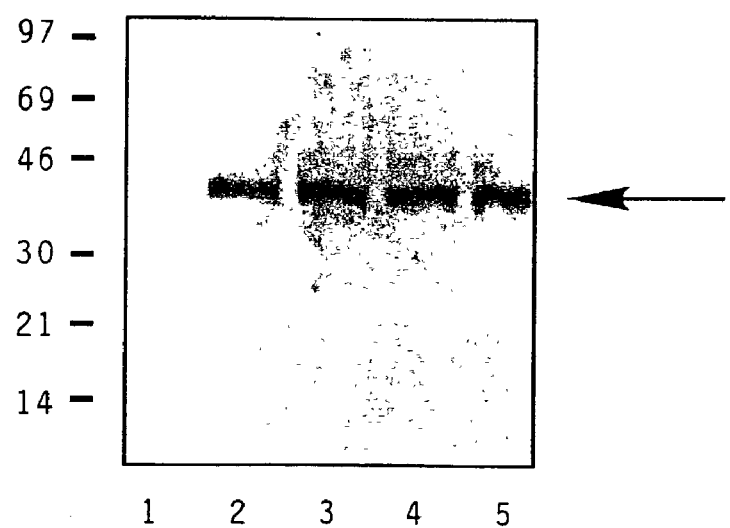
FIG. 1 shows activation of the PKC pathway induces site-specific phosphorylation of NF-IL6/LAP.

12-0-tetradecanoyl-phorbol-13-acetate (TPA) and PKC were used to investigate the post-translational control of NF-IL6/LAP activity. To increase the sensitivity of the system, a CMV-LAP expression vector (Descombes, P., et al., supra, 1990) encoding NF-IL6/LAP was co-transfected into HepG2 hepatoma cells that express negligible amounts of the endogenous protein, in the presence of a PKCα expression vector (James, G., et al., *J. Cell Biol.*, 116:863, 1992). Activation of PKCα by TPA led to a small but reproducible increase in total NF-IL6/LAP phosphorylation (FIG. 1A; compare lanes 3 and 4) but had no effect on its expression level (FIG. 1B). HepG2 cells were transiently transfected with a CMV-LAP expression vector, incubated with [$^{32}$P]-orthophosphate, and $^{32}$P-labelled NF-IL6/LAP was purified by immunoprecipitation using anti-LAP antibodies. The cells were either co-transfected with pUC19 (FIG. 1A, lane 1), pCDM80 (lane 2; empty expression vector) or pCDM8-PKCα (lanes 3 and 4). Cells used in lane 4 were stimulated with TPA (100 ng/ml) for 20 minutes before harvesting.

Figure 1C:
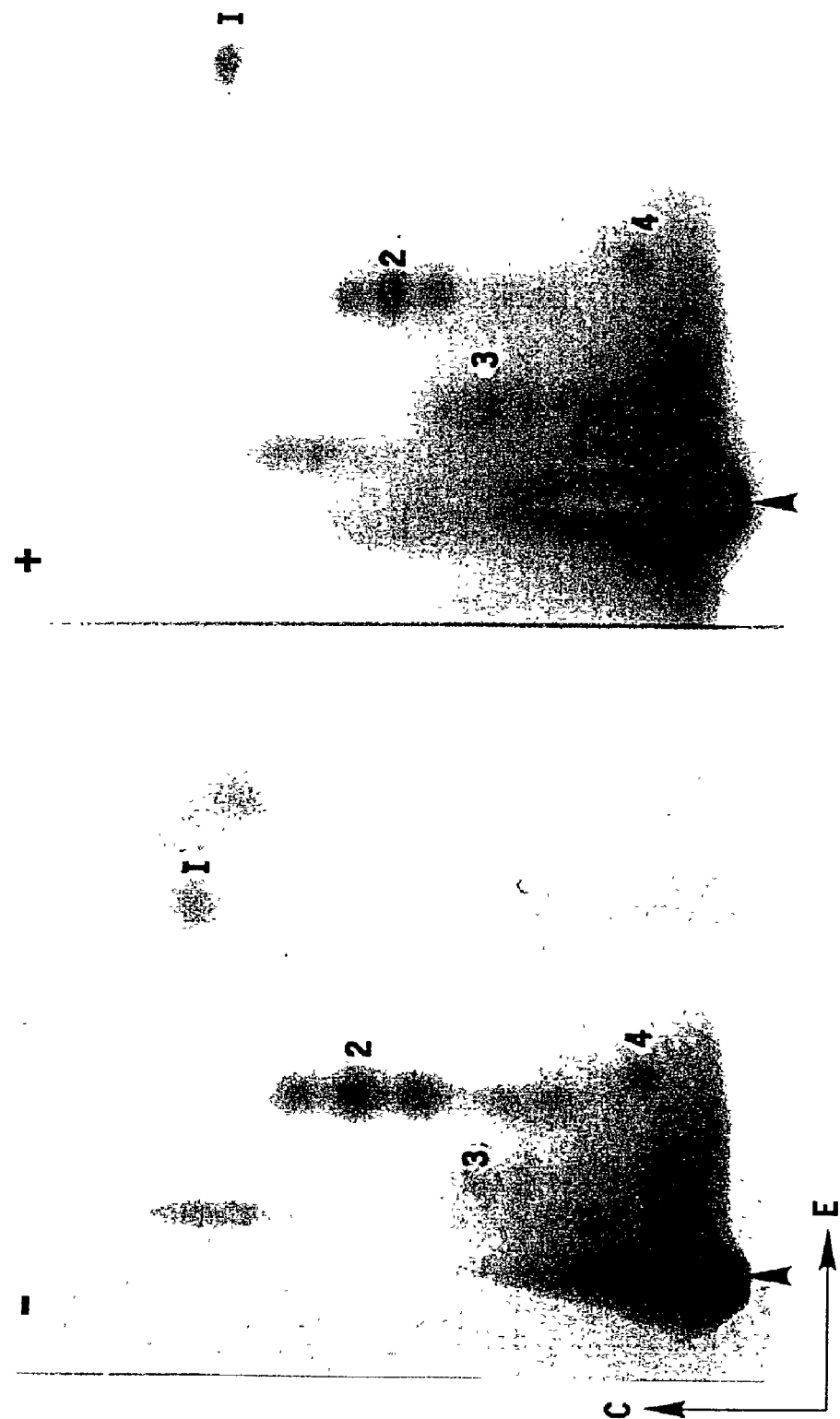

In a parallel experiment, HepG2 cells were either mock transfected (lane 1) or transfected with the CMV-LAP expression vector (lanes 2-5). The cells were co-transfected with pUC19 (lane 2), pCDM8-0 (lane 3) or pCDM8-PKCα (lanes 4 and 5). Cells used in lane 5 were treated or 20 minutes with TPA (100 ng/ml) prior to harvesting. Nuclear extracts were prepared and 10 µg samples were analyzed by Western blotting using anti-LAP antibodies. The immunoblot showed no production of the alternatively translated LIP protein (Descombes, P., et al., supra, 1991), in the presence or absence of PKCα. Two-dimensional tryptic phosphopeptide analysis (Boyle, W. J., et al., *Meth. Enzymol.*, 201:201, 1991) of immunopurified NF-IL6/LAP demonstrated that activation of PKCα by TPA stimulated site-specific phosphorylation of NF-IL6/LAP (FIG. 1C).

Tryptic phosphopeptide maps of in vivo labelled NF-IL6/LAP. Equal amounts of NF-IL6/LAP were isolated from HepG2 cells transfected as described in Panel A (lanes 3 and 4) that were either untreated (−) or treated (+) with TPA, and digested with trypsin. The resultant peptides were separated by high voltage electrophoresis (horizontal dimension) followed by ascending thin layer chromatography (vertical dimension), and visualized by autoradiography. The levels of both phosphopeptides I and 3 were increased after PKC activation. However, only phosphopeptide I was reproducibly increased in response to TPA-treatment of another cell type. Only the reproducible observed NF-IL6/LAP derived phosphopeptides were numbered; other phosphopeptides are most likely derived from contaminating proteins. The arrowhead indicates the origin.

To confirm that both endogenous and transiently expressed NF-L6/LAP are subject to similar changes in their phosphorylation state in a different cell type, these experiments were repeated in a rat fibroblast cell line stably expressing PKCα that was found to express endogenous NF-IL6/LAP. As observed in HepG2 cells, TPA stimulated site-specific phosphorylation of both endogenous and transiently-expressed NF-IL6/LAP. Although the level of several phosphopeptides was increased after TPA treatment, the only change common to both cell-types and affecting both endogenous and transiently expressed NF-IL6/LAP was a higher level of phosphopeptide I (FIG. 1C).

EXAMPLE 2

The PKC Stimulated Phosphorylation Site of NF-IL6/LAP

Mutant NF-IL6/LAP clones containing codons for alanine or aspartic acid at position 105 were produced by standard site directed mutagenesis techniques (See Ausubel, et al., *Current Protocols in Molecular Biology*, Unit 8, Wiley Interscience; 1989). HepG2 Cells were transiently transfected with pCMV-LAP(wt) or pCMV-LAP(Ala105), and labelled with [$^{32}$P]-orthophosphate (2.5 mCi/ml) for 4 h. Following treatment with TPA (100 ng/ml), as described in FIG. 1, cells were lysed in RIPA buffer. Wild type and mutant NF-IL6/LAP were isolated from equal amounts of cell lysates by immunoprecipitation with anti-LAP antibodies (Descombes, P., et al., supra, 1990). After tryptic digest, peptides were separated by two-dimensional electrophoresis as described in Example 1, FIG. 1.

Figure 2:
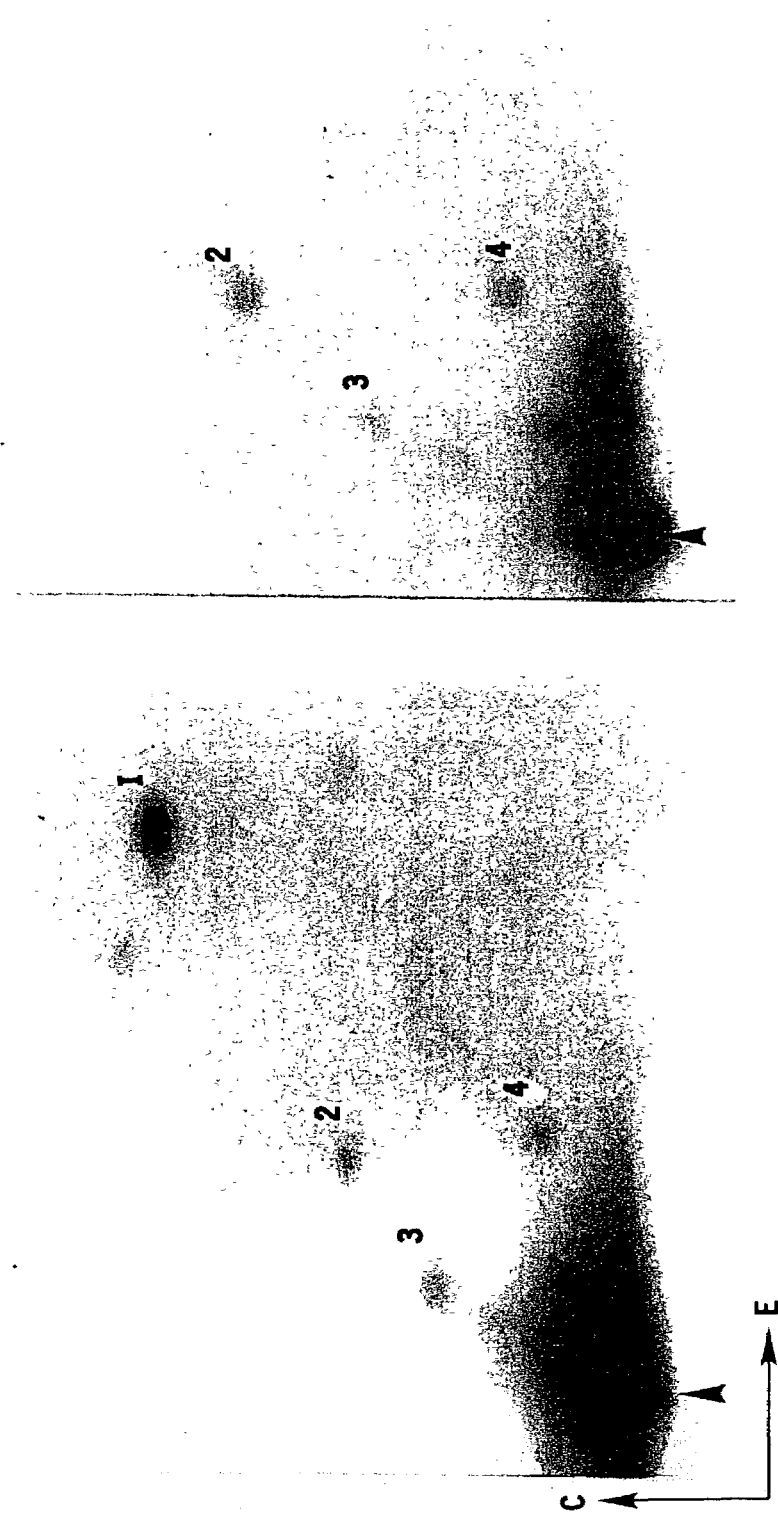
FIG. 2 shows a two-dimensional gel electrophoresis analysis of HepG2 cells transfected with pCMV-LAP(wt) or pCMV-LAP(Ala105) and treated with TPA.

The migration position of phosphopeptide I appeared identical to that of the phosphopeptide which in previous experiments was found to contain Ser105 as its phosphoacceptor. To determine whether Ser105 is indeed a TPA-responsive phosphorylation site, the codon was substituted with an alanine codon. Vectors expressing wild type (wt) NF-IL6/LAP or NF-IL6/LAP(Ala105) were transfected into HepG2 cells and the resultant proteins were isolated after in vivo labelling with [$^{32}$P]-orthophosphate. As shown in FIG. 2, substitution of Ser105 by Ala prevented the appearance of phosphopeptide I.

EXAMPLE 3

Activation by NF-IL6/LAP After Ser105 Phosphorylation

Figure 3A:
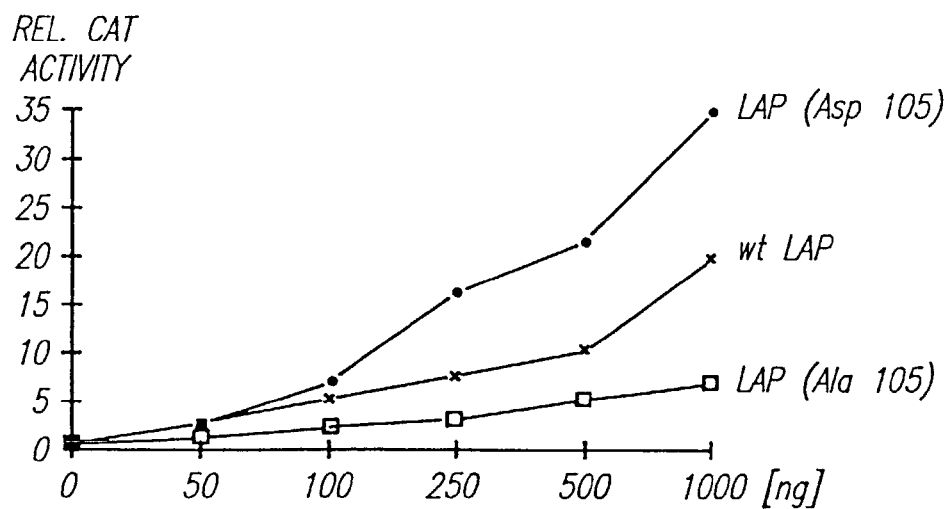
FIG. 3A shows CAT activity for HepG2 cells co-transfected with a CAT reporter plasmid and pCMV-LAP(wt), pCMV-LAP(Ala105), and pCMV-LAP(Asp) plasmids; 3B shows CAT activity for HepG2 cells co-transfected with a CAT reporter plasmid and pCMV-LAP(wt), pCMV-LAP (Ala105), pCDM8 and pCDM8-PKCα, serum starved and stimulated with TPA; 3C shows a mobility shift assay for HepG2 cells co-transfected with pCDM8-0, pCMV-LAP (wt)+pCDM8PKCα, pCMV-LAP(Ala105)+pCDM8-0, and pCMV-LAP(Asp105)+pCDM8-0.
Figure 3B:
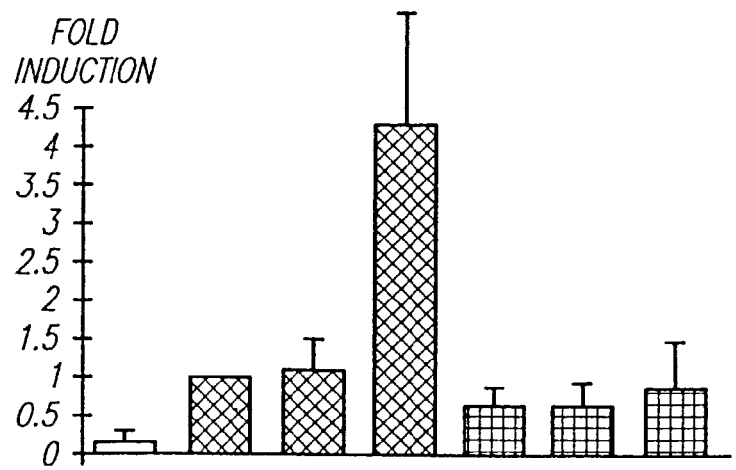
FIG. 3 shows results of CAT assays to show that phosphorylation of serine 105 enhances its activation function.
Figure 3C:
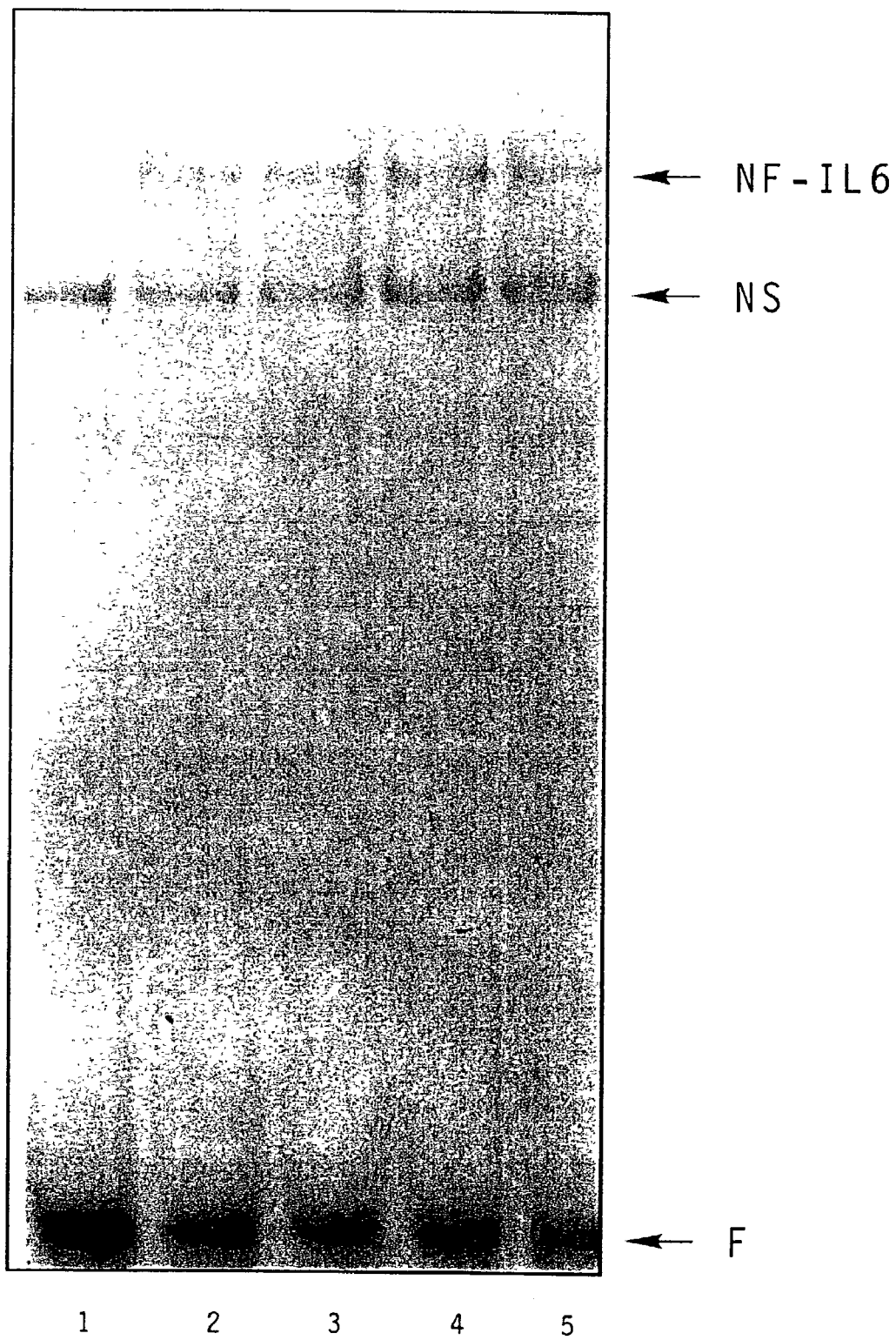
Figures 1, 3D:
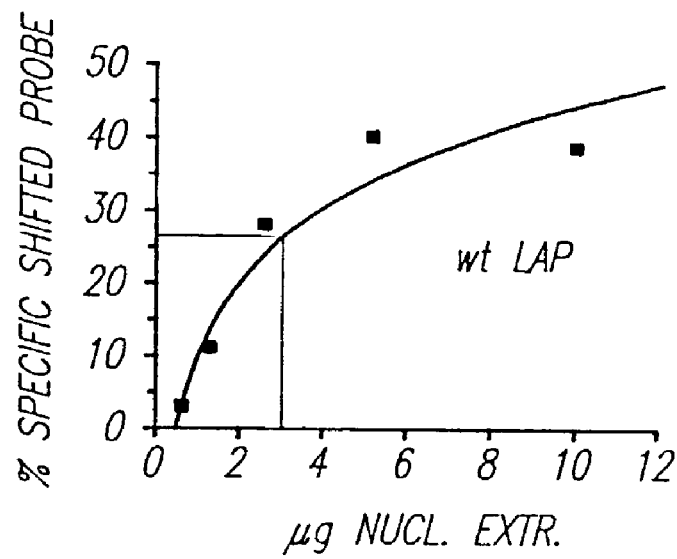
Figures 2, 3D:
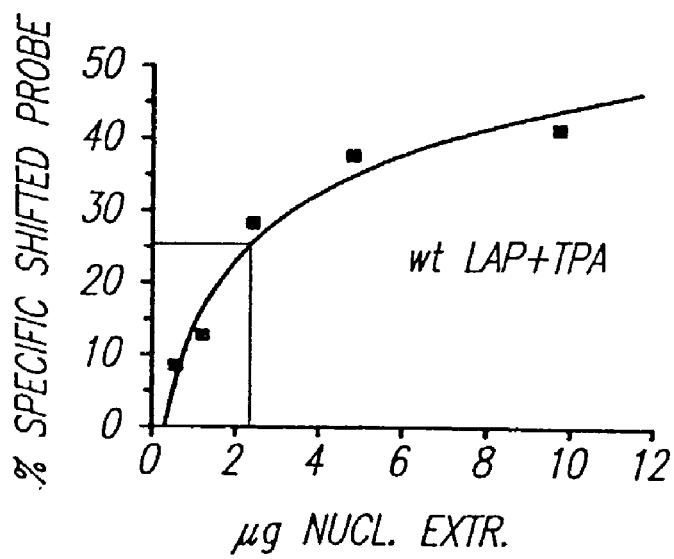
Figures 3, 3D:
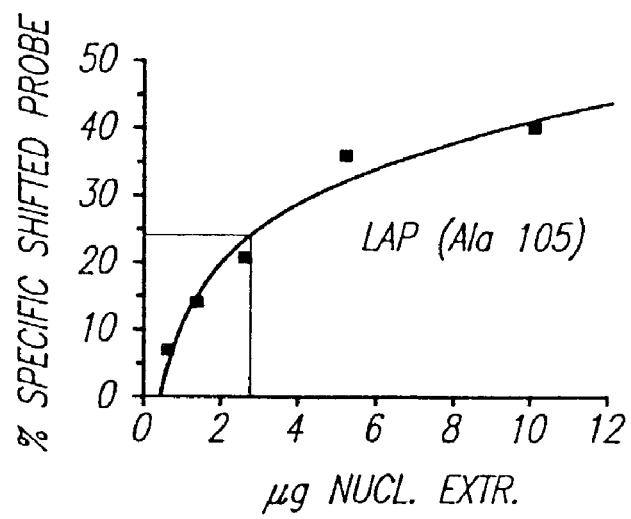

Following identification of Ser105 as the major TPA-responsive phosphorylation site, the effect of its phosphorylation on NF-IL6/LAP activity was studied. The ability of wt NF-IL6/LAP to activate a NF-IL6/LAP-responsive reporter gene was compared with the ability of an Ala105 mutant to activate the reporter gene (FIG. 3).

Three µg of the NF-IL6/LAP-responsive D-CAT reporter plasmid (Descombes, P., et al., supra, 1990; Muller, C. R., et al., *Cell*, 61:279, 1990) were co-transfected into HepG2 cells with increasing amounts of pCMV-LAP(wt), pCMV-LAP (Ala105) and pCMV-LAP(Asp105) expression vectors. Forty-eight hours later the cells were harvested and CAT activity was determined. The results shown are the averages of three experiments (FIG. 3A).

In a second experiment, HepG2 cells were co-transfected with 3 µg of the D-CAT reporter and pCMV-LAP(wt), pCMV-LAP(Ala105). pCDM8 and pCDM8-PKCα expression vectors (1 µg each), as indicated. Serum-starved cells were stimulated with TPA (100 ng/ml), as indicated, 20 hour after transfection. Cells were harvested 40 hour after transfection and CAT expression was measured. The results shown are the averages of three experiments (FIG. 3B).

Next, HepG2 cells were co-transfected with 1 μg each of pCDM8-0 (lane 1), pCMV-LAP(wt)+pCDM8-PKCα (lanes 2 & 3), pCMV-LAP(Ala105)+pCDM8-0 (lane 4), pCMV-LAP(Asp105)+pCDM8-0 (lane 5). Nuclear extracts of the cells were prepared 20 hr after transfection. The cells in lane 3 were stimulated with TPA (100 ng/ml) 20 min prior to harvesting. Mobility shift assays were performed using 15 pg of a $^{32}$P-labelled oligonucleotide spanning the D-site (oligo D) of the albumin promoter (Descombes, P., et al., supra, 1990). The migration positions of the NF-IL6/LAP and non-specific (NS) protein-DNA complexes are indicated, as well as the free (F) probe. The figure shows a representative gel shift assay where approximately 10% of the probe was specifically shifted by NF-IL6/LAP (FIG. 3C).

In another experiment, a fixed amount (15 pg) of the $^{32}$P-labelled oligo D was incubated with increasing amounts of nuclear extracts (in μg) under the same conditions shown above. The fraction of the specifically bound probe was quantified by an Ambis gel scanner and plotted as a function of amount of nuclear extract. The amount of nuclear extracts required to give 50% occupancy is indicated (FIG. 3D).

After washing the cells twice with ice-cold phosphate-buffer saline, nuclear extracts were prepared with minor modifications according to Dignam, et al., (*Nucleic Acids Res.,* 11:1475, 1983). Nuclear extracts were incubated with a $^{32}$P-labelled oligonucleotide spanning the D-site of the albumin promoter as described earlier (Descombes, P., et al., supra, 1990). Free DNA and DNA-protein complexes were resolved on a 6% polyacrylamide gel.

To assess whether increased activity of NF-IL6/LAP following phosphorylation of Ser105 is due to enhanced DNA-binding affinity, mobility shift assays were performed. Increasing amounts of nuclear extracts of cells transfected with the various NF-IL6/LAP vectors were incubated with a $^{32}$P-labelled oligonucleotide spanning the NF-IL6/LAP recognition sequence. Specific binding was markedly increased by transient transfection of both wt and mutant NF-IL6/LAP expression vectors (FIG. 3C). TPA-treatment and the substitution of Ser105 by Ala or Asp had no effect on DNA binding activity (FIG. 3D). Specificity of binding was demonstrated by competition and antibody super-shift experiments.

Although both proteins (wt and Ala105) were expressed (FIG. 3C) and translocated to the nucleus at very similar levels, the wt protein was a more efficient activator of a CAT-reporter linked to a NF-IL6/LAP recognition sequence (Akira, S., et al., *Embo J.,* 9:1897, 1990; Descombes, P., et al., supra, 1990; Muller, C. R., et al., supra, 1990) than the Ala105 mutant (FIG. 3A). Co-transfection of the wt NF-IL6/LAP expression vector with a PKCα expression vector, and TPA treatment resulted in a 5-fold increase in transactivation, while transactivation by NF-IL6/LAP(Ala105) was not affected FIG. 3B. The effect of Ser105 phosphorylation on transactivation can be mimicked by introduction of a negatively charged residue; a mutant NF-IL6/LAP(Asp105) is several-fold more potent as an activator than the wt protein (FIG. 3A). These results strongly suggest that phosphorylation of Ser105 affects the activation function of NF-IL6/LAP.

EXAMPLE 4

Phosphorylation of SER105 Potentiates the Activation Function of NF-IL6/LAP

Figures 3, 3D, 4:
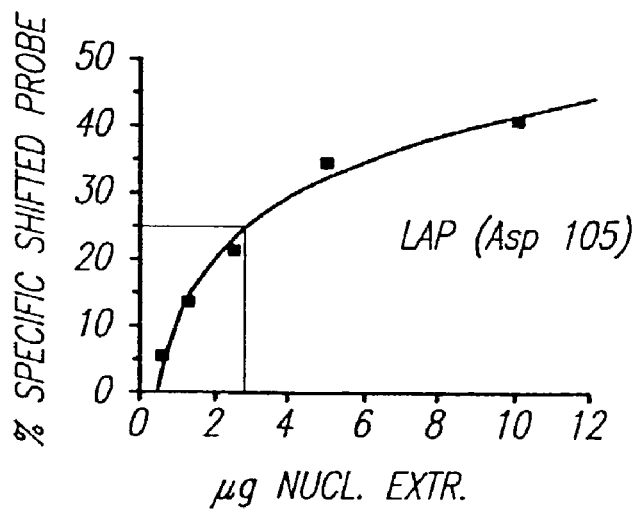

To confirm the phosphorylation of Ser105 potentiates the activation function of NF-IL6/LAP, both the wt and mutant versions (i.e., Ala105, Asp15 of the N-terminal activation domain (Descombes, P., et al., supra, 1991) were fused to the GAL4 DNA-binding domain (Sadowski, I., et al., *Nucleic Acids Res.,* 17:7639, 1989) (FIG. 4).

To construct the GAL4 fusion proteins, the NcoI-EcoRI fragments from pET8c-LAP(Ser105) and pET8c-LAP (Ala105) (Descombes, P., et al., supra, 1990), were replaced by the BspHI-EcoRI fragment containing the coding sequence of the GAL4 DNA-binding domain (aa1-147) from a modified version of the pSG424 vector (Sadowski, I., et al., supra, 1989). The chimeric LAP-GAL4 open reading frames were excised by BglII/EcoRI digestion and were cloned into the pSG424 vector from which the GAL4 DNA-binding domain was removed.

The transactivation domain of NF-IL6/LAP (aa 21-144) (solid bar), was ligated to the N-terminus of the yeast GAL4 DNA-binding domain (aa 1-147) (hatched bar) to generate the chimeric activator LAP/GAL4 (FIG. 4A).

Next, the GAL4-responsive reporter 5×GAL4-LUC (3 μg) was co-transfected with increasing amounts of pSV40-LAP(Ser105)/GAL4, pSV40-LAP(Ala105)/GAL4, or pSV40-LAP(Asp105)/GAL4 expression vectors (Descombes, et al., supra). After 40 hr, the cells were harvested and luciferase activity was determined. The maximal luciferase activity produced by the 5×GAL4-LUC reporter co-transfected with pSV40-LAP(Ser105)/GAL4 was considered to be 100%. The results shown are averages of two experiments (FIG. 4B).

The 5×GAL4-LUC reporter (3 μg) was co-transfected with pSV40-LAP(Ser105)/-GAL4 (10 ng), pSV40-LAP (Ala105)/GAL4 (10 ng), pCDM8-PKCα (100 ng) as indicated. After transfection, the cells were serum-starved for 20 hr and then were treated with TPA (100 ng/ml) for 20 hr or left untreated. Cell extracts were prepared and luciferase activity was determined. The results represent the averages of three different experiments (FIG. 4C).

The ability of LAP(Ser105)/GAL4 to activate the GAL4-responsive reporter (5×GAL4-LUC) was very similar to that of LAP (Ala105)/GAL4, and both were 50- to 200-fold more active than the GAL4 DNA-binding domain alone (FIG. 4B). By contrast, LAP(Asp105)/GAL4, was 3-fold more active than LAP (Ser105)/GAL4. The activity of LAP (Ser105)/GAL4 was stimulated 4-fold by activation of PKCα, whereas the activity of LAP(A1a105)/GAL4 was only slightly increased (FIG. 4C). These results demonstrate that the activation potential of NF-IL6/LAP is directly enhanced by phosphorylation of Ser105, an effect mimicked by introduction of a negative charge into that position.

The protein kinase responsible for phosphorylation of Ser105 is unlikely to be PKC itself, because this residue is not phosphorylated by purified PKC in vitro. In addition, a constitutively activated derivative of PKCα that is predominantly nuclear (James, G., et al., *J. Cell Biol.,* 116:863, 1992) does not stimulate NF-IL6/LAP activity or phosphorylation. This derivative, however, is capable of affecting the phosphorylation and activity of other nuclear proteins such as myogenic (U, L, et al., *Cell,* 71:1181, 1992). Most likely, activation of PKC results in activation of downstream protein kinases including the one directly responsible for phosphorylation of NF-IL6/LAP on Ser105. In this invention, PKC activation serves to mimic part of the signalling response which may be elicited by inflammatory mediators.

The foregoing is meant to illustrate, but not to limit, the scope of the invention. Indeed, those of ordinary skill in the art can readily envision and produce further embodiments, based on the teachings herein, without undue experimentation.

The invention claimed is:

1. An isolated polypeptide characterized by:
   (a) having transactivation activity; and
   (b) having the amino acid sequence of a fragment of nuclear factor-interleukin 6/lymphokine activating protein (NF-IL6/LAP) with a modification, wherein:
      (i) the amino acid sequence of the NF-IL6/LAP fragment is set forth in SEQ ID NO:1, and
      (ii) the modification is an amino acid substitution at residue 31 of SEQ ID NO:1 from serine to a negatively charged amino acid.

2. The polypeptide of claim 1, wherein the negatively charged amino acid is selected from the group consisting of glutamic acid and aspartic acid.

3. An isolated synthetic peptide comprising SEQ ID NO: 1, wherein the isolated synthetic peptide contains a modification at residue 31, and wherein the modification at residue 31 is substitution of the residue with a negatively charged amino acid.

4. The peptide of claim 3, wherein the negatively charged amino acid is selected from the group comprising aspartic acid and glutamic acid.

5. An isolated polypeptide characterized by:
(a) having transactivation activity; and
(b) having the amino acid sequence of nuclear factor-interleukin 6/lymphokine activating protein (NF-IL6/LAP) with a modification, wherein:
(i) the amino acid sequence set of NF-IL6/LAP is forth in SEQ ID NO:4, and
(ii) the modification is an amino acid substitution at residue 105 of SEQ ID NO:4 from serine to a negatively charged amino acid.

6. The polypeptide of claim 5, wherein the negatively charged amino acid is selected from the group consisting of glutamic acid and aspartic acid.

* * * * *

SEQUENCE LISTING

<160> NUMBER OF SEQ ID NOS: 4

<210> SEQ ID NO 1
<211> LENGTH: 51
<212> TYPE: PRT
<213> ORGANISM: Rattus norvegicus

<400> SEQUENCE: 1

Ala Asp Phe Ala Ala Pro Ala Pro Ala His His Asp Phe Leu Ser Asp
1               5                   10                  15

Leu Phe Ala Asp Asp Tyr Gly Ala Lys Pro Ser Lys Pro Ser Asp
                20                  25                  30

Tyr Gly Tyr Val Ser Leu Gly Arg Ala Gly Ala Lys Ala Ala Pro Pro
            35                  40                  45

Ala Cys Phe
    50

<210> SEQ ID NO 2
<211> LENGTH: 153
<212> TYPE: DNA
<213> ORGANISM: Rattus norvegicus

<400> SEQUENCE: 2
gcggacttcg ccgcgcccgc gcccgcgcac cacgacttcc tttccgacct cttcgccgac      60
gactacggcg ccaagccgag caagaagccg tccgactacg gttacgtgag cctcggccgc     120
gcgggcgcca aggccgcacc gcccgcctgc ttc                                  153

<210> SEQ ID NO 3
<211> LENGTH: 1739
<212> TYPE: DNA
<213> ORGANISM: Rattus norvegicus
<220> FEATURE:
<221> NAME/KEY: CDS
<222> LOCATION: (127)..(1020) <223>

<400> SEQUENCE: 3 agggccccg gcgtgacgca gcccgttgcc aggcgccgcc ttataaacct ccgctcggcc        60
gccgccgagc cgagtccgag ccgcgcacgg gaccgggacg cagcggagcc cgcgggcccc     120 gcgttc atg cac cgc ctg ctg gcc tgg gac gca gca tgc ctc ccg ccg       168
       Met His Arg Leu Leu Ala Trp Asp Ala Ala Cys Leu Pro Pro
       1               5                   10 ccg ccc gcc gcc ttt aga ccc atg gaa gtg gcc aac ttc tac tac gag      216
Pro Pro Ala Ala Phe Arg Pro Met Glu Val Ala Asn Phe Tyr Tyr Glu
15                  20                  25                  30 ccc gac tgc ctg gcc tac ggg gcc aag gcg gcc cgc gcc gcg ccg cgc      264
Pro Asp Cys Leu Ala Tyr Gly Ala Lys Ala Ala Arg Ala Ala Pro Arg
                35                  40                  45 gcc ccc gcc gcc gag ccg gcc atc ggc gag cac gag cgc gcc atc gac      312
Ala Pro Ala Ala Glu Pro Ala Ile Gly Glu His Glu Arg Ala Ile Asp
                50                  55                  60 ttc agc ccc tac ctg gag ccg ctc gcg ccc gcc gcg gac ttc gcc          360
Phe Ser Pro Tyr Leu Glu Pro Leu Ala Pro Ala Ala Asp Phe Ala
                65                  70                  75

| | | | | | | | | | | | | | | |
|---|---|---|---|---|---|---|---|---|---|---|---|---|---|---|
| gcg | ccc | gcg | ccc | gcg | cac | cac | gac | ttc | ctt | tcc | gac | ctc | ttc | gcc | gac | 408 |
| Ala | Pro | Ala | Pro | Ala | His | His | Asp | Phe | Leu | Ser | Asp | Leu | Phe | Ala | Asp |
| | 80 | | | | 85 | | | | | 90 | | | | | |

```
gcg ccc gcg ccc gcg cac cac gac ttc ctt tcc gac ctc ttc gcc gac     408
Ala Pro Ala Pro Ala His His Asp Phe Leu Ser Asp Leu Phe Ala Asp
         80                  85                  90 gac tac ggc gcc aag ccg agc aag aag ccg tcc gac tac ggt tac gtg     456
Asp Tyr Gly Ala Lys Pro Ser Lys Lys Pro Ser Asp Tyr Gly Tyr Val
 95                 100                 105                 110 agc ctc ggc cgc gcg ggc gcc aag gcc gca ccg ccc gcc tgc ttc ccg     504
Ser Leu Gly Arg Ala Gly Ala Lys Ala Ala Pro Pro Ala Cys Phe Pro
                115                 120                 125 ccg ccg cct ccc gcc gca ctc aag gcc gag ccg ggc ttc gaa ccc gcg     552
Pro Pro Pro Pro Ala Ala Leu Lys Ala Glu Pro Gly Phe Glu Pro Ala
            130                 135                 140 gac tgc aag cgc gcg gac gac gcg ccc gcc atg gcg gcc ggc ttc ccg     600
Asp Cys Lys Arg Ala Asp Asp Ala Pro Ala Met Ala Ala Gly Phe Pro
        145                 150                 155 ttc gcc ctg cgc gcc tac ctg ggc tac cag gcg acg ccg agc ggc agc     648
Phe Ala Leu Arg Ala Tyr Leu Gly Tyr Gln Ala Thr Pro Ser Gly Ser
    160                 165                 170 agc ggc agc ctg tcc acg tcg tcg tcg tcc agc ccg ccc ggg acg ccg     696
Ser Gly Ser Leu Ser Thr Ser Ser Ser Ser Ser Pro Pro Gly Thr Pro
175                 180                 185                 190 agc ccc gcc gac gcc aag gcc gcg ccc gcc gcc tgc ttc gcg ggg ccg     744
Ser Pro Ala Asp Ala Lys Ala Ala Pro Ala Ala Cys Phe Ala Gly Pro
                195                 200                 205 ccg gcc gcg ccc gcc aag gcc aag gcc aag aag gcg gtg gac aag ctg     792
Pro Ala Ala Pro Ala Lys Ala Lys Ala Lys Lys Ala Val Asp Lys Leu
            210                 215                 220 agc gac gag tac aag atg cgg cgc gag cgc aac aac atc gcg gtg cgc     840
Ser Asp Glu Tyr Lys Met Arg Arg Glu Arg Asn Asn Ile Ala Val Arg
        225                 230                 235 aag agc cgc gac aag gcc aag atg cgc aac ctg gag acg cag cac aag     888
Lys Ser Arg Asp Lys Ala Lys Met Arg Asn Leu Glu Thr Gln His Lys
    240                 245                 250 gtg ctg gag ctg acg gcg gag aac gag cgg ctg cag aag aag gtg gag     936
Val Leu Glu Leu Thr Ala Glu Asn Glu Arg Leu Gln Lys Lys Val Glu
255                 260                 265                 270 cag ctg tcg cga gag ctc agc acg ctg cgg aac ttg ttc aag cag ctg     984
Gln Leu Ser Arg Glu Leu Ser Thr Leu Arg Asn Leu Phe Lys Gln Leu
                275                 280                 285 ccc gag ccg ctg ctg gcc tcg gcg ggt cac tgc tag cccggcgggg         1030
Pro Glu Pro Leu Leu Ala Ser Ala Gly His Cys
            290                 295 gtggcgtggg ggcgccgcgg ccaccctggg caccgtgcgc cctgccccgc gcgctccgtc   1090
cccgcgcgcg cccgggcacc gtgcgtgcac gcgcgcacc tgcacctgca ccagggggac    1150
accgtgggca ccgcgcgcac gcacctgcac cgcgcaccgg gtttcgggac ttgatgcaat   1210
ccggatcaaa cgtggctgag cgcgtgtgga cacgggactg acgcaacaca cgtgtaactg   1270
tcagccgggc cctgagtaat cacttaaaga tgttcctgcg gggttgttgc tgttgatgtt   1330 tttcttttg ttttttgttt tttgttttttt ttttggtctt attatttttt tgtattatat    1390
aaaaaagttc tatttctatg agaaagagg cgtatgtata ttttgagaac cttttccgtt    1450
tcgagcatta aagtgaagac attttaataa acttttttgg agaatgttta aaaacctttt   1510
gggggcagta gttggctttt gaaaaaaaat ttttttttctt ccctcctgac tttggattta  1570
tgcgagattt tgttttttgt gtttctggtg tgtaggggc tgcgggtat ttttggggttg   1630 tgtgtggtgg tgggtgggg tgtcgcatct gggttttttct cctcccctgg cagatgggat  1690
```

-continued

```
gccagcccct ccccccagga gaggggcag agtgccgggt caggaattc    1739
```

<210> SEQ ID NO 4
<211> LENGTH: 297
<212> TYPE: PRT
<213> ORGANISM: Rattus norvegicus

<400> SEQUENCE: 4

```
Met His Arg Leu Leu Ala Trp Asp Ala Ala Cys Leu Pro Pro Pro
1               5                   10                  15

Ala Ala Phe Arg Pro Met Glu Val Ala Asn Phe Tyr Tyr Glu Pro Asp
            20                  25                  30

Cys Leu Ala Tyr Gly Ala Lys Ala Ala Arg Ala Ala Pro Arg Ala Pro
                35                  40                  45

Ala Ala Glu Pro Ala Ile Gly Glu His Glu Arg Ala Ile Asp Phe Ser
        50                  55                  60

Pro Tyr Leu Glu Pro Leu Ala Pro Ala Ala Asp Phe Ala Ala Pro
65                  70                  75                  80

Ala Pro Ala His His Asp Phe Leu Ser Asp Leu Phe Ala Asp Asp Tyr
                85                  90                  95

Gly Ala Lys Pro Ser Lys Lys Pro Ser Asp Tyr Gly Tyr Val Ser Leu
                100                 105                 110

Gly Arg Ala Gly Ala Lys Ala Ala Pro Pro Ala Cys Phe Pro Pro Pro
            115                 120                 125

Pro Pro Ala Ala Leu Lys Ala Glu Pro Gly Phe Glu Pro Ala Asp Cys
    130                 135                 140

Lys Arg Ala Asp Asp Ala Pro Ala Met Ala Ala Gly Phe Pro Phe Ala
145                 150                 155                 160

Leu Arg Ala Tyr Leu Gly Tyr Gln Ala Thr Pro Ser Gly Ser Ser Gly
                165                 170                 175

Ser Leu Ser Thr Ser Ser Ser Ser Pro Pro Gly Thr Pro Ser Pro
            180                 185                 190

Ala Asp Ala Lys Ala Ala Pro Ala Ala Cys Phe Ala Gly Pro Pro Ala
        195                 200                 205

Ala Pro Ala Lys Ala Lys Ala Lys Lys Ala Val Asp Lys Leu Ser Asp
    210                 215                 220

Glu Tyr Lys Met Arg Arg Glu Arg Asn Asn Ile Ala Val Arg Lys Ser
225                 230                 235                 240

Arg Asp Lys Ala Lys Met Arg Asn Leu Glu Thr Gln His Lys Val Leu
                245                 250                 255

Glu Leu Thr Ala Glu Asn Glu Arg Leu Gln Lys Lys Val Glu Gln Leu
            260                 265                 270

Ser Arg Glu Leu Ser Thr Leu Arg Asn Leu Phe Lys Gln Leu Pro Glu
        275                 280                 285

Pro Leu Leu Ala Ser Ala Gly His Cys
    290                 295
```